(12) United States Patent
Miyamoto (10) Patent No.: US 8,805,041 B2
(45) Date of Patent: Aug. 12, 2014

(54) X-RAY IMAGE PROCESSING APPARATUS, X-RAY IMAGE PROCESSING METHOD, AND STORAGE MEDIUM FOR COMPUTER PROGRAM

(75) Inventor: Hideaki Miyamoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 92 days.

(21) Appl. No.: 13/515,677

(22) PCT Filed: Dec. 10, 2010

(86) PCT No.: PCT/JP2010/072732
§ 371 (c)(1),
(2), (4) Date: Jun. 13, 2012

(87) PCT Pub. No.: WO2011/074657
PCT Pub. Date: Jun. 23, 2011

(65) Prior Publication Data
US 2012/0257809 A1    Oct. 11, 2012

(30) Foreign Application Priority Data

Dec. 16, 2009 (JP) .................... 2009-285763

(51) Int. Cl.
*G06K 9/00* (2006.01)
(52) U.S. Cl.
USPC .......................................... 382/130; 382/274
(58) Field of Classification Search
CPC ........... G06T 5/007; G06T 5/008; G06T 5/50; G06T 7/0085; G06T 2207/10116; G06T 2207/20012; G06T 2207/20224; G06T 2207/30101; G06T 2207/30104; G06K 2209/05; A61B 6/481; A61B 6/504; G01R 33/56; G01R 33/563; G01R 33/5635
USPC ........... 382/128, 130, 132, 274; 378/62, 98.7, 378/98.12
See application file for complete search history.

(56) References Cited

U.S. PATENT DOCUMENTS

| | | | |
|---|---|---|---|
| 5,056,524 A | 10/1991 | Oe | 128/654 |
| 5,285,786 A | 2/1994 | Fujii | 128/653.1 |
| 2004/0081342 A1* | 4/2004 | Sato | 382/128 |
| 2007/0183637 A1 | 8/2007 | Kreuzer et al. | 382/128 |
| 2008/0051648 A1 | 2/2008 | Suri et al. | 600/407 |

(Continued)

FOREIGN PATENT DOCUMENTS

| | | | | |
|---|---|---|---|---|
| DE | 102006025917 A1 | 12/2007 | | A61B 6/00 |
| JP | 61-058639 A | 3/1986 | | A61B 6/00 |

(Continued)

OTHER PUBLICATIONS

Seeram, et al., "Image Postprocessing in Digital Radiology—A Primer for Technologists", Journal of Medical Imaging and Radiation Sciences, (2008), pp. 23-41, vol. 39.

(Continued)

*Primary Examiner* — Andrew W Johns
(74) *Attorney, Agent, or Firm* — Canon USA, Inc. IP Division (57) ABSTRACT

A feature value is extracted from a boundary region that is located between a contrast-agent injection region and a background region in a subtraction image, a gradation curve depending on the feature value is generated, and gradation processing is performed by applying the gradation curve to the subtraction image.

15 Claims, 4 Drawing Sheets

(56) References Cited

U.S. PATENT DOCUMENTS

| | | | |
|---|---|---|---|
| 2008/0137935 A1* | 6/2008 | Spahn | 382/132 |
| 2008/0285853 A1 | 11/2008 | Bressan | 382/169 |
| 2009/0010512 A1* | 1/2009 | Zhu et al. | 382/130 |

FOREIGN PATENT DOCUMENTS

| | | | | |
|---|---|---|---|---|
| JP | 64-017631 A | 1/1989 | | A61B 6/00 |
| JP | H01-109483 A | 4/1989 | | |
| JP | 04364677 A | 12/1992 | | H04N 5/325 |
| JP | 06251127 A | 9/1994 | | G06F 15/62 |
| JP | 2002344806 A | 11/2002 | | H04N 5/325 |
| JP | 2008061763 A | 3/2008 | | A61B 6/00 |

OTHER PUBLICATIONS

Gronenschild, et al., "Quantitative Angiography on a Macintosh II", IEEE, Sep. 23, 1990, pp. 133-136.

Chu, et al., "A Novel Gray-Level Registration Algorithm for DSA Image Based on Subtraction Histogram", IEEE, (2006).

Leu, Jia-Guu, "Image Contrast Enhancement Based on the Intensities of Edge Pixels", Graphical Models and Image Processing, Nov. 1992, pp. 497-506, vol. 54, No. 6.

\* cited by examiner

X-RAY IMAGE PROCESSING APPARATUS, X-RAY IMAGE PROCESSING METHOD, AND STORAGE MEDIUM FOR COMPUTER PROGRAM

TECHNICAL FIELD

The present invention relates to gradation processing for an image that is obtained by digital subtraction angiography.

BACKGROUND ART

Since digital techniques have progressed in recent years, in many cases, digital processing is performed for images even in medical fields. Instead of conventional radiography using a film for X-ray diagnosis, a two-dimensional X-ray sensor that outputs an X-ray image as a digital image is being widely used. Digital image processing, such as gradation processing, is becoming more important for the digital image output by the two-dimensional X-ray sensor.

An example of the digital image processing is digital subtraction angiography (hereinafter, referred to as "DSA"). The DSA analyzes X-ray images before and after a contrast agent is injected, by using a computer, and reconfigures only an image of blood vessels with the contrast agent injected. This method does not need a conventional special treatment. Merely by injecting the contrast agent from a vein, a sharp image of blood vessels of the entire body can be obtained. Hence, the method can be performed even for an outpatient. This method is becoming more important for clinical sites. A DSA image that is obtained by the DSA is obtained such that images are acquired before and after the contrast agent is injected into an object, and the image before the contrast agent is injected (hereinafter, referred to as "mask image") is subtracted from the image after the contrast agent is injected (hereinafter, referred to as "live image"). In the subtraction processing of the mask image from the live image, a blood vessel region, which is a region of interest for the diagnosis, is held as a change region between the images caused by the injection of the contrast agent, and the other unnecessary region is eliminated as a background region to obtain a uniform region. Thus, the generated DSA image is useful for the diagnosis.

Meanwhile, the DSA image has a pixel-value distribution that is significantly different from that of the original live image or mask image. More specifically, image information is concentrated in a very narrow area with respect to a pixel-value area of the entire image, whereas a noise or the like having a small information amount is dispersed in the pixel-value area other than that narrow area. Owing to this, if the gradation processing, like the processing performed for the typical X-ray image to increase the contrast, is applied to the DSA image, a wide gradation range is assigned to the region with the noise or the like having the small information amount, but a gradation range is insufficiently assigned to the useful region for the diagnosis, resulting in the contrast being improper. The gradation processing performed for the DSA image has to be different from the gradation processing performed for the typical X-ray image, and has to take the pixel-value distribution of the DSA image into account.

Conventionally, an X-ray fluoroscopy apparatus has performed gradation processing such as window processing, in which an operator uses an operation panel to adjust a window width and a window level while the operator checks a monitor. Unfortunately, the window processing through the manual operation by the operator is typically a troublesome work. It is difficult to quickly and properly perform the adjustment. In addition, the processing result may vary depending on an operator. To address this problem, widely performed is a method that obtains a feature value through analysis of the subtraction image, which is obtained by subtracting the mask image from the live image, and performs the gradation processing on the basis of the feature value.

Japanese Patent Laid-Open No. 01-017631 discloses a method that obtains image enhanced-characteristic information based on a maximum gradation value and a peak value or a bottom value, which are obtained through histogram analysis performed for a subtraction image, and uses the image enhanced-characteristic information for the window processing. Also, Japanese Patent Laid-Open No. 61-058639 discloses processing that acquires a peak value through histogram analysis, adjusts the peak value to match a predetermined reference value, and hence corrects a base pixel value of a subtraction image.

With these methods, since the feature value of the gradation processing is obtained by analyzing the subtraction image, the gradation processing suitable for the pixel-value distribution unique to the DSA image can be performed. In particular, these methods are effective to automatically adjust the gradation of the entire image to fall within a constant range suitable for the diagnosis.

A wide region of the DSA image is the background region having the uniform pixel value. The impression of the entire image depends on the pixel-value range within which the pixel value of the background range falls. The purpose of use of the DSA image, in view of the diagnosis, is observation of the blood vessel region. Hence, it is desirable to increase visibility of the region with the contrast agent injected.

With the conventionally typically used methods based on the histogram analysis, although a stable image having the gradation of the entire image falling within the constant range can be obtained, the conventional methods do not include an idea for the increase in visibility of the region with the contrast agent, the region which is particularly important for the diagnosis.

CITATION LIST

Patent Literature

PTL 1 Japanese Patent Laid-Open No. 01-017631 Japanese Patent Laid-Open No. 61-058639

SUMMARY OF INVENTION

The present invention is made in light of the situations. According to an aspect of the present invention, an X-ray image processing apparatus includes an inter-image subtracting unit configured to acquire a subtraction image by performing subtraction processing among a plurality of X-ray images that are obtained when an image of an object is captured at different times; a first-feature-value extracting unit configured to extract a first feature value from a contrast-agent injection region in the subtraction image; and a gradation conversion processing unit configured to perform gradation conversion processing for the subtraction image by using a gradation curve based on the first feature value.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodi

DESCRIPTION OF EMBODIMENTS

Preferred embodiment(s) of the present invention will be described in detail in accordance with the accompanying drawings.

Components described in the embodiment(s) are merely examples. The technical scope of the present invention is determined by the claims, but is not limited by the individual embodiment(s) given below.

Embodiment

An X-ray image processing apparatus according to an embodiment of the present invention will be described below with reference to FIG. 1. An X-ray image processing apparatus 100 includes an X-ray generating unit 101 that can generate X-ray pulses by 3 to 30 pulses per second, and a two-dimensional X-ray sensor 104 that receives X-rays 103 transmitted through an object 102 and captures a movie that is synchronized with the X-ray pulses. The two-dimensional X-ray sensor 104 functions as an image pickup unit configured to capture a movie of the object 102 that is irradiated with the X-rays.

The X-ray image processing apparatus 100 includes an inter-image subtraction processing unit 107 that subtracts a mask image stored in an image storage unit 106 from an X-ray image after a contrast agent is injected (hereinafter, referred to as "live image"), the X-ray image being output by a pre-processing unit 105, and that outputs the result as a subtraction image. The X-ray image processing apparatus 100 includes a gradation processing unit 108 that performs gradation processing for each frame of the subtraction image output by the inter-image subtraction processing unit 107, and an image display unit 109 that displays an image after the gradation process, as a DSA image.

The configuration of the gradation processing unit 108 is the most featured configuration in this embodiment, and will be described in detail with reference to a block diagram in FIG. 2.

The gradation processing unit 108 includes a first-feature-value extracting unit 201 that extracts a first feature value, and a second-feature-value extracting unit 202 that extracts a second feature value, from each frame of the subtraction image. The gradation processing unit 108 also includes a gradation-curve generating unit 203 that generates a gradation curve on the basis of the first and second feature values, and a gradation conversion processing unit 204 that performs gradation conversion processing for each frame of the subtraction image by using the generated gradation curve.

Figure 3:
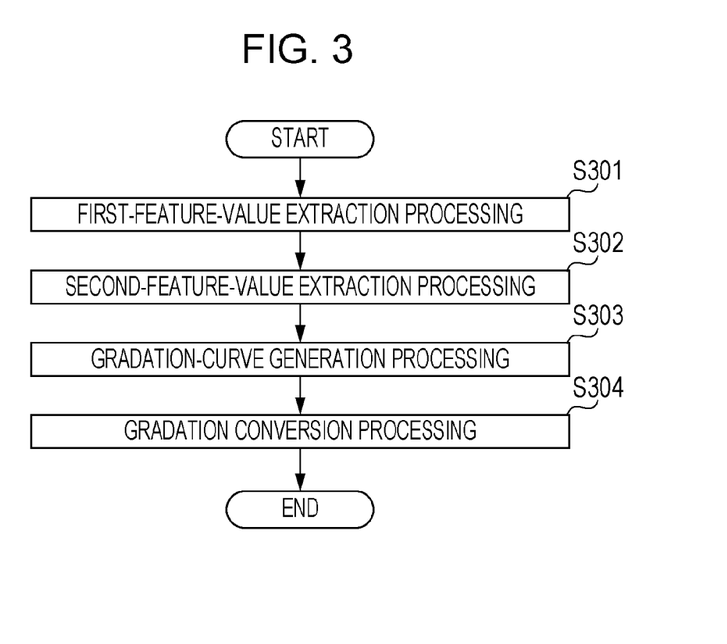
FIG. 3 illustrates a processing flow by the gradation processing unit.

The operation of the gradation processing unit 108 having the above configuration will be further described below with reference to a flowchart in FIG. 3.

In step S301, the gradation processing unit 108 inputs the subtraction image that is output by the inter-image subtraction processing unit 107 to the first-feature-value extracting unit 201. The first-feature-value extracting unit 201 outputs the first feature value.

In step S302, the gradation processing unit 108 inputs the subtraction image that is output by the inter-image subtraction processing unit 107 to the second-feature-value extracting unit 202. The second-feature-value extracting unit 202 outputs the second feature value.

In step S303, the gradation processing unit 108 inputs the first feature value output by the first-feature-value extracting unit 201 and the second feature value output by the second-feature-value extracting unit 202 to the gradation-curve generating unit 203. The gradation-curve generating unit 203 outputs the gradation curve.

In step S304, the gradation processing unit 108 inputs the subtraction image output by the inter-image subtraction processing unit 107 and the gradation curve output by the gradation-curve generating unit 203 to the gradation conversion processing unit 204. The gradation conversion processing unit 204 outputs the display DSA image after the graduation processing. The gradation processing unit 108 ends this flow.

The first-feature-value extracting unit 201 extracts a region for calculating the first feature value. The contrast of this region should be enhanced when the gradation processing is performed for the subtraction image. This region is obtained on the basis of a contrast-agent injection region. In particular, extracting a region with a large change in contract from the subtraction image is effective, because, if visibility of the region with the large change in contrast of the contrast-agent injection region increases, this region is useful for the diagnosis. Also, in many cases, the region with the large change in contrast frequently may belong to a predetermined range in the contrast-agent injection region, the range which extends from the boundary between the contrast-agent injection region and a background region. Thus, this region is extracted. Then, the first-feature-value extracting unit 201 calculates the first feature value, which is a representative pixel value of a pixel group in the extracted region.

Figure 4:
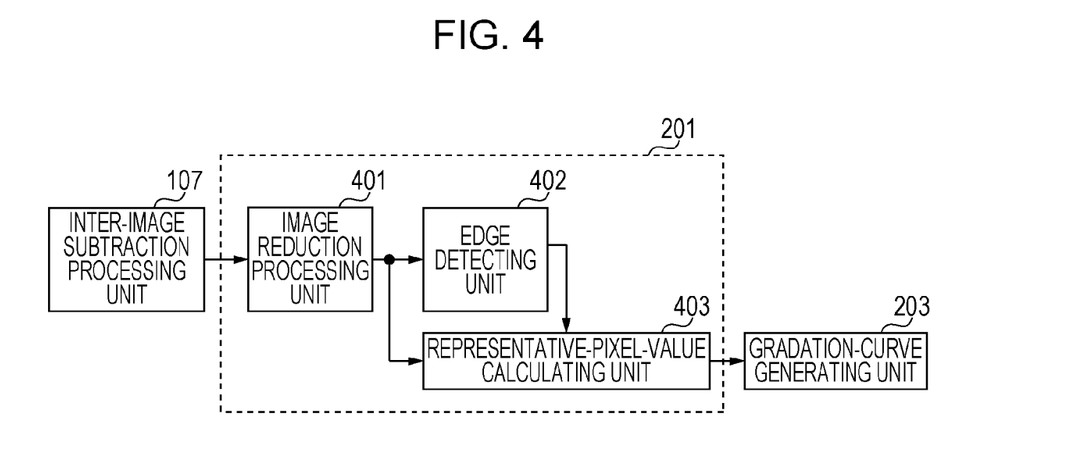
FIG. 4 illustrates a detailed configuration of a first-feature-value extracting unit.

Various methods can be used as the method for extracting the first feature value. FIG. 4 is a block diagram showing an example of the first-feature-value extracting unit 201 that outputs the first feature value as the result of the input of the subtraction image and includes an image reduction processing unit 401, an edge detecting unit 402, and a representative-pixel-value calculating unit 403. The operation of the first-feature-value extracting unit 201 with this configuration will be described with reference to a flowchart in FIG. 5.

Figure 5:
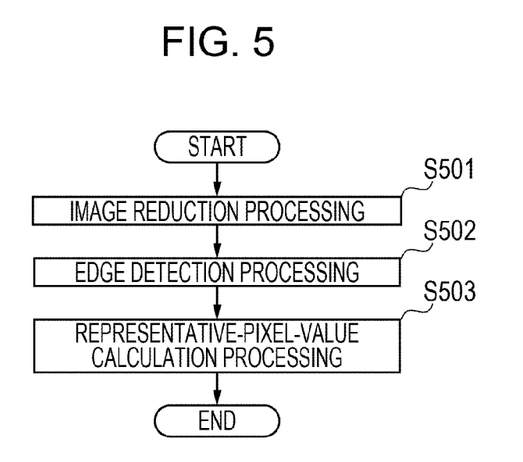
FIG. 5 illustrates a processing flow by the first-feature-value extracting unit.

In step S501, the first-feature-value extracting unit 201 inputs the subtraction image $I_S$ output by the inter-image subtraction processing unit 107 to the image reduction processing unit 401. The image reduction processing unit 401 outputs a reduced image $I_R$. The reduced image $I_R$ is an image obtained such that the input subtraction image $I_S$ is divided into predetermined-size blocks, and an average value of each block is determined as a value of a single pixel. In the following processing, the reduced image $I_R$ is a subject for the processing, to increase the processing speed and to reduce the influence of a noise present in the subtraction image $I_S$.

In step S502, the first-feature-value extracting unit 201 inputs the reduced image $I_R$ to the edge detecting unit 402. The edge detecting unit 402 generates an edge image $I_E$. The edge image $I_E$ is a binary image including 1 indicative of a pixel that belongs to the boundary between the contrast-agent injection region and the background region, and 0 indicative of the other pixel. The edge image $I_E$ is generated by, for example, the Canny edge detection method (described later).

In step S503, the first-feature-value extracting unit 201 inputs the reduced image $I_R$ and the edge image $I_E$ to the representative-pixel-value calculating unit 403. The representative-pixel-value calculating unit 403 outputs a representative pixel value. The representative pixel value is, for example, an average value of a pixel group in the reduced image $I_R$ including a predetermined pixel value or larger, the pixel group corresponding to pixels in a predetermined range in the edge image $I_E$, the range extending from pixels whose pixel values are 1.

In this case, the region within the predetermined range from the boundary between the contrast-agent injection region and the background region is extracted from the contrast-agent injection region, and an average value of that region can be obtained. The predetermined pixel value is determined by a value in the background image of the subtraction image. Under equivalent image-capturing conditions, the value of the background image in the subtraction image is substantially 0. By changing the predetermined range in accordance with the change in contrast, a region in accordance with the degree of the change in contrast can be extracted.

The representative pixel value is, for example, a pixel value equivalent to a histogram peak when a pixel-value histogram is generated for the pixel group in the reduced image $I_R$ corresponding to the pixels whose pixel values are 1 in the edge image $I_E$. Alternatively, an average pixel value of the pixel group in the reduced image $I_R$ corresponding to the pixels whose pixel values are 1 may be used. The first-feature-value extracting unit 201 outputs the representative value as the first feature value, and ends the processing. In this case, since the representative value is calculated from the boundary between the contrast-agent injection region and the background region, the representative value can be used for the region with the large change in contrast. This representative value is useful because the change in contrast of the boundary region between the contrast-agent injection region and the background region tends to be large.

Figure 6:
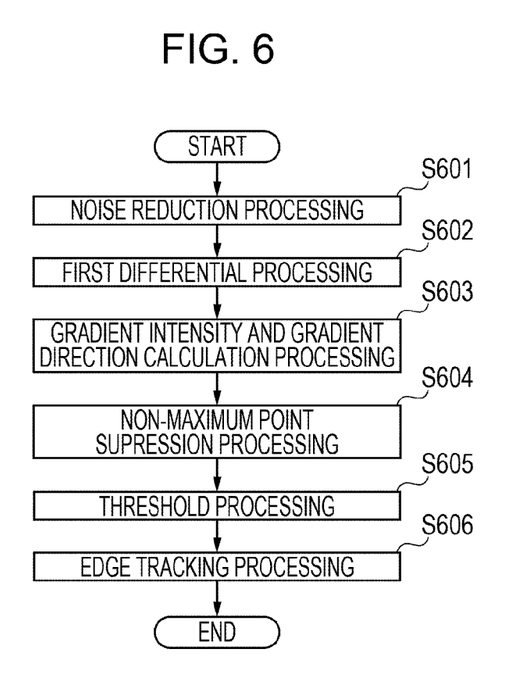
FIG. 6 illustrates a flow of edge detection processing.

Next, the Canny edge detection method will be described with reference to a flowchart in FIG. 6, as an example of the edge detection processing executed by the edge detecting unit 402.

In step S601, the edge detecting unit 402 performs noise reduction processing for the input reduced image $I_R$ by a Gaussian filter, to generate a noise-reduced image $I_N$.

In step S602, the edge detecting unit 402 performs first differential processing in the horizontal and vertical directions for the noise-reduced image $I_N$ by using an edge detecting operator, such as the Roberts operator, the Prewitt operator, or the Sobel operator, to generate a horizontal differential image Gx and a vertical differential image Gy. The horizontal differential image Gx and the vertical differential image Gy are images whose pixel values have information about gradient intensities and gradient directions in the horizontal and vertical directions.

A first differential value is calculated from a difference between pixel values of pixels. The contrast of the contrast-agent injection region changes in an initial phase, a middle phase, and a final phase of the injection of the contrast agent. To deal with this, the distance between the pixels, from which the first differential value is calculated, may be changed with regard to an elapsed time since the contrast agent is ejected. The distance between the pixels may be increased because the contrast is lowered in the initial and final phases.

Also, the contrast of the contrast-agent injection region changes depending on the diameter and hardness of the blood vessel. Owing to this, the distance between the pixels, from which the first differential value is calculated, may be changed in accordance with the attribute of the object.

To automatically change the distance between the pixels, from which the first differential value is calculated, an additional value of absolute values of the pixels in the contrast-agent injection region may be obtained. The magnitude of the additional value is highly correlated with the contrast of the contrast-agent injection region. As the additional value is larger, the contrast becomes higher. Thus, the distance between the pixels, from which the first differential value is calculated, is decreased.

In step S603, the edge detecting unit 402 calculates a gradient intensity image G and a gradient direction image θ with the following expressions by using the horizontal differential image Gx and the vertical differential image Gy.

$$G = \sqrt{Gx^2 + Gy^2} \quad \text{[Math. 1]}$$

$$\theta = \arctan\left(\frac{Gy}{Gx}\right) \quad \text{[Math. 2]}$$

The gradient intensity image G is an image in which pixel values represent gradient intensities. The gradient direction image θ is an image in which pixel values represent gradient directions such that, for example, in the noise-reduced image $I_N$, the gradient directions are expressed by values in a range from $-\pi/2$ (inclusive) to $\pi/2$ (exclusive), the values including 0 indicative of a pixel whose pixel value increases in the horizontal direction and $\pi/2$ indicative of a pixel whose pixel value increases in the vertical direction.

In step S604, the edge detecting unit 402 performs non-maximum point suppression processing based on the gradient intensity image G and the gradient direction image θ, and outputs a potential edge image E. The potential edge image E is a binary image including 1 indicative of a local maximum edge pixel in the noise-reduced image and 0 indicative of the other pixel. In the non-maximum point suppression processing, two adjacent pixels of a target pixel (x, y) are selected on the basis of the gradient direction image θ(x, y). If a gradient intensity image G(x, y) of the target pixel (x, y) is larger than the values of the two adjacent pixels, the target pixel (x, y) is considered as a local maximum edge pixel, and is expressed as E(x, y)=1. A specific example is described as follows.

If the gradient direction image θ(x, y) is in a range from $-\pi/8$ (inclusive) to $\pi/8$ (exclusive), E(x, y) is determined by the following expression while two pixels arranged in the horizontal direction serve as the adjacent pixels.

$$E(x, y) = \begin{cases} 1 & (G(x-1, y) < G(x, y) \text{ and } G(x, y) < G(x+1, y)) \\ 0 & \text{(Other than those above)} \end{cases} \quad \text{[Math. 3]}$$

If the gradient direction image θ(x, y) is in a range from $\pi/8$ (inclusive) to $3\pi/8$ (exclusive), E(x, y) is determined by the following expression while two pixels arranged in an oblique direction serve as the adjacent pixels.

$$E(x, y) = \begin{cases} 1 & (G(x, y) > G(x-1, y-1) \text{ and } G(x, y) > G(x+1, y+1)) \\ 0 & \text{(Other than those above)} \end{cases}$$ [Math. 4]

If the gradient direction image θ(x, y) is in a range from 3π/8 (inclusive) to π/2 (exclusive) or a range from −π/2 (inclusive) to −3π/8 (exclusive), E(x, y) is determined by the following expression while two pixels arranged in the vertical direction serve as the adjacent pixels.

$$E(x, y) = \begin{cases} 1 & (G(x, y) > G(x, y-1) \text{ and } G(x, y) > G(x, y+1)) \\ 0 & \text{(Other than those above)} \end{cases}$$ [Math. 5]

If the gradient direction image θ(x, y) is in a range from −3π/8 (inclusive) to −π8 (exclusive), E(x, y) is determined by the following expression while two pixels arranged in an oblique direction serve as the adjacent pixels.

$$E(x, y) = \begin{cases} 1 & (G(x, y) > G(x-1, y+1) \text{ and } G(x, y) > G(x+1, y-1)) \\ 0 & \text{(Other than those above)} \end{cases}$$ [Math. 6]

In step S605, the edge detecting unit 402 performs threshold processing for the potential edge image E on the basis of the gradient intensity image G and two thresholds $T_{low}$ and $T_{high}$ ($T_{low}<T_{high}$), and outputs a low edge image $E_{low}$ and a high edge image $E_{high}$. The low edge image $E_{low}$ is a binary image including, when gradient intensity images G(x, y) are respectively compared with values $T_{low}$ for all pixels (x, y) that satisfy potential edge image E(x, y)=1, 1 indicative of a pixel that satisfies G(x, y)>$T_{low}$ and 0 indicative of the other pixel. The high edge image $E_{high}$ is a binary image including, when gradient intensity images G(x, y) are respectively compared with values $T_{high}$ for all pixels (x, y) that satisfy potential edge image E(x, y)=1, 1 indicative of a pixel that satisfies G(x, y)>$T_{high}$, and 0 indicative of the other pixel.

In step S606, the edge detecting unit 402 performs edge tracking processing on the basis of the low edge image $E_{low}$ and the high edge image $E_{high}$, and outputs an edge image $I_E$. In the edge tracking processing, if a connected component of the pixels (x, y) that satisfy low edge image $E_{low}$(x, y)=1 includes pixels (x, y) that satisfy high edge image $E_{high}$(x, y)=1, all pixels (x, y) included in the connected component are considered as edge pixels, which are expressed by $I_E$(x, y)=1. The other pixels (x, y) are non-edge pixels, which are expressed by $I_E$(x, y)=0. The edge image $I_E$ acquired by the above processing is output as the result of the Canny edge detection method, and the Canny edge detection processing is ended.

The boundary between the contrast-agent injection region and the background region, the boundary which is the subject for the edge detection according to this embodiment, has an edge characteristic that varies depending on the injection state of the contrast agent. Hence, in the edge detection processing, the operator used for the noise reduction processing or the first differential processing may be properly changed depending on the time since the injection of the contrast agent is started. If the frame rate during the image capturing is high, to increase the processing speed, part of the noise reduction processing, threshold processing, or edge tracking processing may be omitted or replaced with relatively simple processing. Another example of the edge detection processing may be a method for detecting zero-crossing on the basis of second differential processing.

The second feature value extracted by the second-feature-value extracting unit 202 is a pixel value in the background region that occupies a wide area of the subtraction image that is brought within a predetermined pixel-value range between frames or different captured images by the gradation processing.

The second feature value is acquired such that the characteristic for occupying the wide area of the image is used, for example, a histogram of the subtraction image is generated, and a peak pixel value is obtained. If images output by the pre-processing unit 105 before and after the injection of contrast agent are stable, the histogram analysis may not be performed, and the pixel value in the background region of the subtraction image may be 0. If a plurality of pixel values each having a maximum frequency that is larger than a predetermined frequency are present, a maximum pixel value may be selected as the second feature value from among the plurality of pixel values.

When the histogram is generated from the subtraction image, the subtraction image may be reduced to a predetermined size. Alternatively, a predetermined pixel-value range may be grouped as a single pixel value and then a histogram may be generated.

The gradation-curve generating unit 112 generates a gradation curve by using the first and second feature values that are obtained by the aforementioned method. The gradation curve generated herein is expressed by a sigmoid function with the following expression, for example, when x and y are pixel values of images before and after the gradation conversion processing.

$$y = \frac{1}{1 + \exp(-a(x-b))}$$ [Math. 7]

In the above expression, values a and b are parameters for the gradation conversion processing when the sigmoid function is used as the gradation curve. The value a is the degree of contrast enhancement, and the value b is a pixel value for which highest contrast enhancement is performed by the gradation conversion processing. In this embodiment, the gradation curve is generated by obtaining these values on the basis of the first and second feature values.

When x1 is a pixel value represented by the first feature value and x2 is a pixel value represented by the second feature value, and if the pixel value after the gradation conversion, the pixel value which is represented by the second feature value, is substituted to Expression 1 as a predetermined pixel value y2, the parameters a and b can be obtained by Expressions 8 and 9 as follows.

$$b = x1$$ [Math. 8]

$$a = -\frac{\log(1/y2 - 1)}{x2 - x1}$$ [Math. 9]

The gradation conversion processing unit 113 applies, as the gradation curve, the sigmoid function (Expression 4), which is obtained by substituting the parameters a and b obtained with Expressions 8 and 9 to Expression 1, to the subtraction image, and the gradation conversion processing is performed. At this time, when x is a pixel value of the subtraction image, a pixel value y of the display DSA image after the gradation conversion can be obtained by the following expression.

$$y = \frac{1}{1 + \exp\left(\frac{\log(1/y2 - 1)}{x2 - x1}(x - x1)\right)} \quad [\text{Math. 10}]$$

The value y in Expression 10 is within a range from 0 to 1. Hence, the value y is multiplied by a predetermined value (for example, 255), so that the value corresponds to a display gradation. With Expression 8, the value of a pixel value x1 after the gradation conversion processing becomes 0.5. In general, the pixel value x1 represented by the first feature value is smaller than the pixel value x2 represented by the second feature value. Hence, if the value y2 is larger than 0.5, an image including a bright background region and a dark contrast-agent injection region can be obtained. In contrast, to obtain an image including a dark background region and a bright contrast-agent injection region, the value y2 may be smaller than 0.5.

With this embodiment, the feature values are extracted respectively from the boundary between the contrast-agent injection region and the background region and from the background region of the subtraction region, and the gradation processing is performed on the basis of the feature values. Accordingly, separation performance is increased by enhancing the contrast at the boundary between the contrast-agent injection region important for the diagnosis and the background region. Also, the gradation processing suitable for the DSA image can be automatically performed such that the pixel values in the background region are brought within the pixel-value range proper for the diagnosis.

Figure 1:
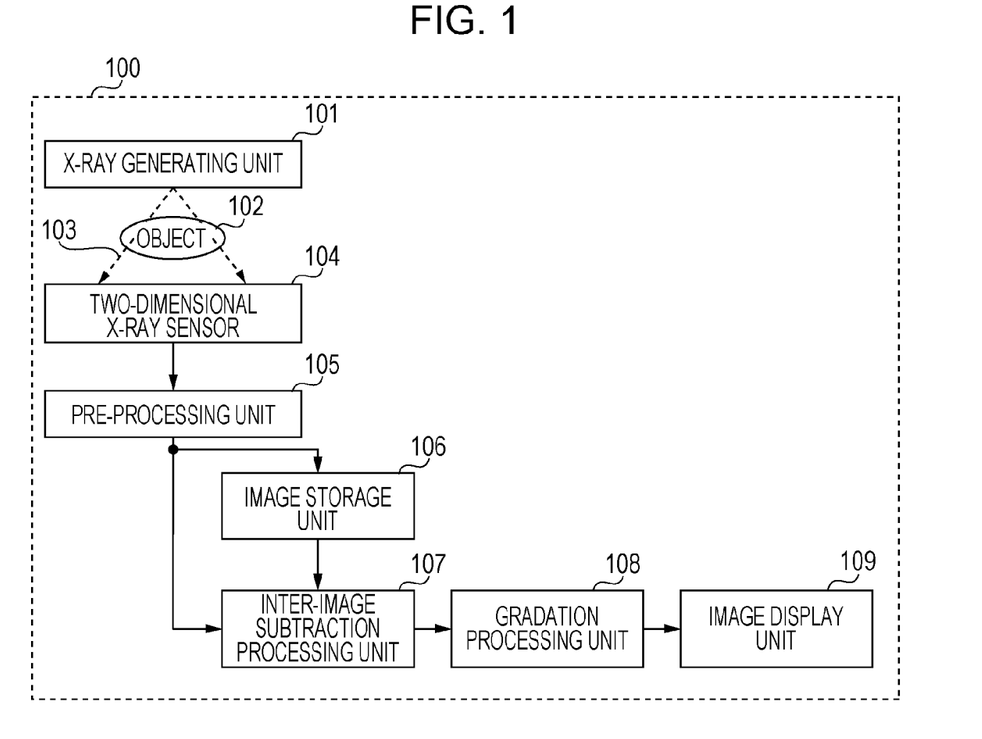
- FIG. 1 illustrates a configuration of an X-ray image processing apparatus according to a first embodiment.
Figure 2:
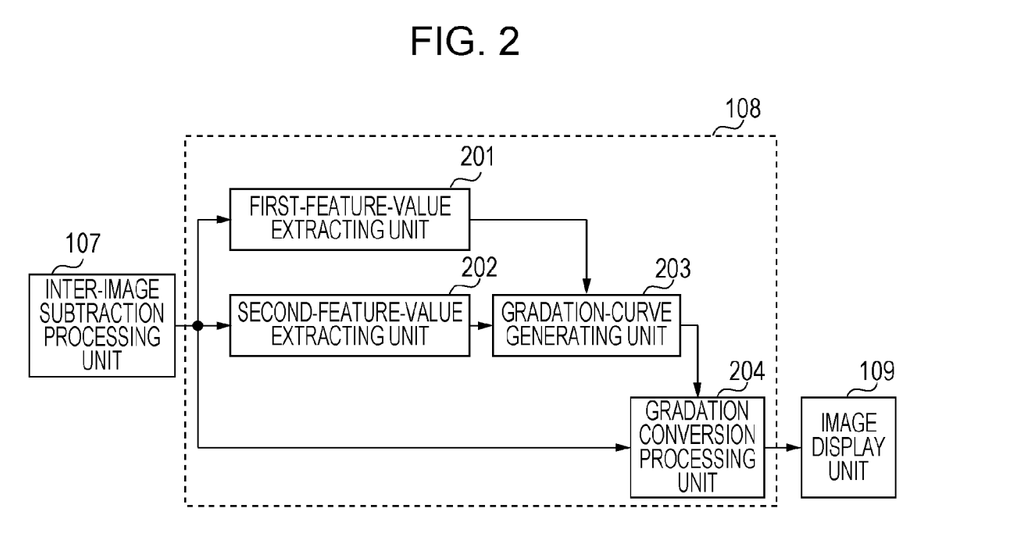
FIG. 2 illustrates a detailed configuration of a gradation processing unit.

The units shown in FIGS. 1 and 2 may be formed by dedicated hardware configurations. Alternatively, functions of the hardware configurations may be provided by software. In this case, the functions of the units shown in FIGS. 1 and 2 can be provided by installing the software in an information processing device and by executing the software to provide an image processing method through an arithmetic operation function of the information processing device. Through the execution of the software, for example, the mask image and the live image before and after the contrast agent is injected are acquired by the pre-processing for respective frames of the movie output by the two-dimensional X-ray sensor 104, and the subtraction image is acquired by the inter-image subtracting step. Then, the gradation processing step is executed such that the first and second feature values are extracted from the subtraction image, the gradation curve is generated, and the gradation conversion processing is performed.

Figure 7:
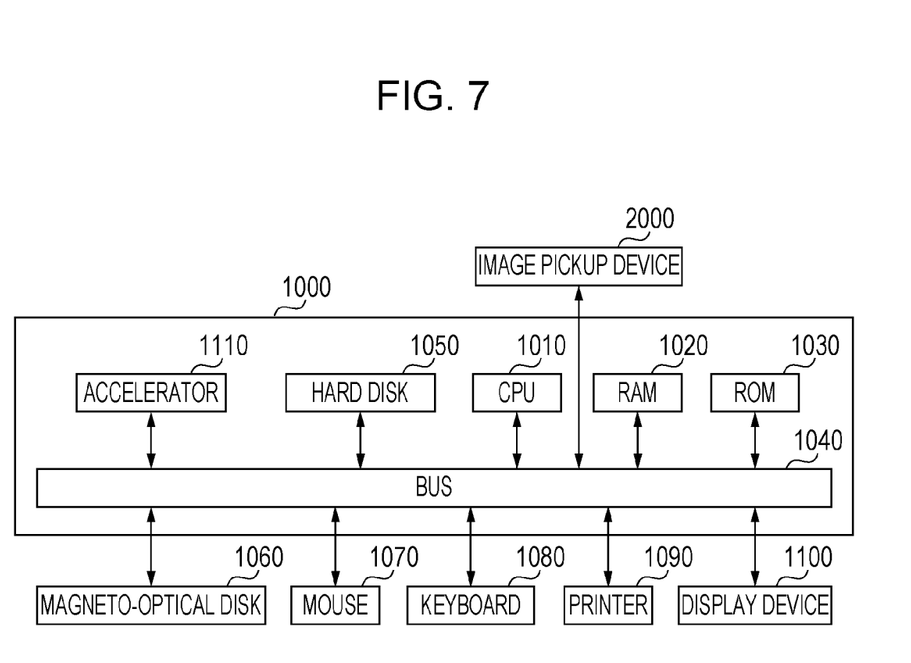
FIG. 7 illustrates an exemplary computer system that can provide the present invention.

FIG. 7 is a block diagram showing a hardware configuration of the information processing device and peripheral devices thereof. An information processing device 1000 is connected with an image pickup device 2000 such that data communication can be made therebetween.

Information Processing Device

A CPU 1010 controls the entire information processing device 1000 by using a computer program and data stored in a RAM 1020 and a ROM 1030. Also, the CPU 1010 executes arithmetic processing relating to X-ray image processing that is predetermined by the execution of the computer program.

The RAM 1020 includes an area for temporarily storing a computer program and data loaded from a magneto-optical disk 1060 or a hard disk 1050. The RAM 1020 also includes an area for temporarily storing image data such as the mask image, live image, and subtraction image, acquired from the image pickup device 2000. The RAM 1020 further includes a work area that is used when the CPU 1010 executes various processing. The ROM 1030 stores setting data and a boot computer program of the information processing device 1000.

The hard disk 1050 holds an operating system (OS), and a computer program and data for causing the CPU 1010 to execute the processing of the respective units shown in FIGS. 1 and 2. The held contents are loaded to the RAM 1020 properly under the control by the CPU 1010, and become subjects for the processing by the CPU 1010. In addition, the hard disk 1050 can save the data of the mask image, live image, and subtraction image.

The magneto-optical disk 1060 is an example of an information storage medium. The magneto-optical disk 1060 can store part of or all the computer program and data saved in the hard disk 1050.

When an operator of the information processing device 1000 operates a mouse 1070 or a keyboard 1080, the mouse 1070 or the keyboard 1080 can input various instructions to the CPU 1010.

A printer 1090 can print out an image, which is displayed on the image display unit 109, onto a recording medium.

A display device 1100 is formed of a CRT or a liquid crystal screen. The display device 1100 can display the processing result of the CPU 1010 by images and characters. For example, the display device 1100 can display the image processed by the respective units shown in FIGS. 1 and 2 and finally output from the image display unit 109. In this case, the image display unit 109 functions as a display control unit configured to cause the display device 1100 to display an image. A bus 1040 connects the respective units in the information processing device 1000 with each other to allow the respective units to exchange data.

Image Pickup Device

Next, the image pickup device 2000 will be described. The image pickup device 2000 can capture the movie during the injection of the contrast agent like the X-ray fluoroscopy apparatus. The image pickup device 2000 transmits the captured image data to the information processing device 1000. Plural pieces of image data may be collectively transmitted to the information processing device 1000. Alternatively, image data may be transmitted successively in order of capturing.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-285763, filed Dec. 16, 2009, which is hereby incorporated by reference herein in its entirety.

The invention claimed is:

1. An image processing apparatus comprising:
   a subtractor configured to acquire a subtraction image by performing subtraction processing among a plurality of radiographic images that are obtained when an image of an object is captured at different times;
   a first-feature-value extractor configured to extract a first feature value based on a boundary region between a contrast-agent injection region and a background region in the subtraction image; and a convertor configured to perform gradation conversion for the subtraction image based on the first feature value.

2. The image processing apparatus according to claim 1, wherein the first-feature-value extractor acquires a region, from which the first feature value is extracted, on the basis of a value indicative of a contrast of the subtraction image.

3. The image processing apparatus according to claim 1, wherein the first-feature-value extractor is configured to calculate a first differential value from a difference between pixel values of pixels in the subtraction image, and to acquires a region, from which the first feature value is extracted, on the basis of the first differential value.

4. The image processing apparatus according to claim 3, wherein the first-feature-value extractor is configured to change a distance between the pixels for the calculation of the first differential value, on the basis of an absolute value of a pixel value in the contrast-agent injection region.

5. The image processing apparatus according to claim 1, wherein the first-feature-value extractor includes an edge detector configured to detect an edge in the subtraction image by performing edge detection processing for the subtraction image, and acquires the first feature value from a pixel that belongs to the edge.

6. The image processing apparatus according to claim 5, wherein the first-feature-value extractor is configured to use the Canny edge detection method.

7. The image processing apparatus according to claim 5, wherein the first-feature-value extractor is configured to use a plurality of edge detecting operators, and to select one of the operators in accordance with an injection state of a contrast agent.

8. The image processing apparatus according to claim 1, wherein the first-feature-value extractor is configured to change processing in accordance with a frame rate during the capturing of the radiographic images for the object.

9. The image processing apparatus according to claim 1, wherein the first-feature-value extractor is configured to calculate, as the first feature value, an average pixel value in a region extracted from the subtraction image.

10. The image processing apparatus according to claim 1, further comprising:
a second-feature-value extractor configured to extract a second feature value from a region that is a background region of the subtraction image,
wherein the gradation curve used in the gradation conversion is based on the first and second feature values.

11. The image processing apparatus according to claim 10, wherein the second-feature-value extractor is configured to generate a histogram for pixels that belong to an edge in the subtraction image, and to calculates the second feature value on the basis of the histogram.

12. The image processing apparatus according to claim 10, wherein the second-feature-value extractor is configured to output 0 as the second feature value if image-capturing conditions for the radiographic images of the object before and after the contrast agent is injected are equivalent to each other.

13. The image processing apparatus according to claim 1, wherein the radiographic images obtained when the image of the object is captured at the different times are images before and after the contrast agent is injected.

14. An image processing method comprising:
a subtracting step of acquiring a subtraction image by performing subtraction processing among a plurality of radiographic images that are obtained when an image of an object is captured at different times;
a first-feature-value extracting step of extracting a first feature value based on a boundary region between a contrast-agent injection region and a background region in the subtraction image; and
a converting step of performing gradation conversion for the subtraction image by using a gradation curve based on the first feature value.

15. A non-transitory computer-readable storage medium storing a computer program that causes a computer to execute the image processing method according to claim 14.

* * * * *